United States Patent [19]

Hill

[11] 4,093,719

[45] June 6, 1978

[54] ANTIARTHRITIC COMPOSITIONS COMPRISING BIS[(TRIALKYL-PHOSPHINE)GOLD(I)]SULFIDES AND METHODS OF PRODUCING ANTIARTHRITIC ACTIVITY

[75] Inventor: David Taylor Hill, North Wales, Pa.

[73] Assignee: SmithKline Corporation, Philadelphia, Pa.

[21] Appl. No.: 769,245

[22] Filed: Feb. 16, 1977

[51] Int. Cl.$^2$ ............................................ A61K 31/66
[52] U.S. Cl. .................................................. 424/215
[58] Field of Search ...................... 424/215; 260/430

[56] References Cited

U.S. PATENT DOCUMENTS

| | | | |
|---|---|---|---|
| 3,676,554 | 7/1972 | McGusty et al. | 260/330 |
| 3,718,679 | 2/1973 | McGusty et al. | 260/430 |
| 3,718,680 | 2/1973 | McGusty et al. | 260/430 |

OTHER PUBLICATIONS

Aust. J. Chem. 19, pp. 547–554, (1966).

*Primary Examiner*—Stanley J. Friedman
*Attorney, Agent, or Firm*—Joseph A. Marlino; Richard D. Foggio; William H. Edgerton

[57] ABSTRACT

Pharmaceutical compositions having antiarthritic activity comprising Bis[(Trialkylphosphine)Gold(I)]Sulfides and methods of producing antiarthritic activity by administering internally, preferably orally, said compositions.

4 Claims, No Drawings

ANTIARTHRITIC COMPOSITIONS COMPRISING BIS[(TRIALKYL-PHOSPHINE)GOLD(I)]SULFIDES AND METHODS OF PRODUCING ANTIARTHRITIC ACTIVITY

This invention relates to novel pharmaceutical compositions having antiarthritic activity and to methods of producing antiarthritic activity by administering said compositions. More specifically, the compositions of this invention comprise bis[(trialkylphosphine)gold(I)]sulfide as the active medicament.

The novel pharmaceutical compositions of this invention, in dosage unit form, comprise a nontoxic pharmaceutical carrier and a bis[(trialkylphosphine)gold(I)]sulfide represented by the following structural formula:

$$(R_3P \rightarrow Au)_2 S$$

Formula 1 wherein:

R represents lower alkyl being straight or branched chain of from 1 to 4 carbon atoms.

The compounds of Formula 1 are either known or are prepared by methods known in the literature. For example, the appropriately substituted trialkylphosphinegold in a non-reactive organic solvent is mixed with aqueous sodium sulfide. The solution is evaporated to dryness and recrystallized to give the desired bis phosphines. Reference may be made to Aust. J. Chem. 19, 547, 1966.

The antiarthritic activity of the compositions of this invention is measured by the ability of the active medicament to inhibit adjuvant-induced polyarthritis in rats. The active medicaments of Formula 1 produce marked inhibition of the development of adjuvant arthritis in rats at daily oral doses as low as 20 mg. (calculated on gold content) per kilogram of body weight. Adjuvant arthritis in rats is produced by a single injection of 0.75 mg. of *Mycobacterium butyricum* suspended in white paraffin (N.F.) into a hindpaw (left footpad). The injected paw becomes inflamed and reaches a maximum volume in three to five days (primary lesion). The animals exhibit a decrease in body weight gain during this initial period. Adjuvant arthritis (secondary phase) occurs after a delay of approximately ten days and is characterized by inflammation of the non-injected sites (right hind leg), decrease in body weight gain and further increases in the volume of the injected hind leg. The compounds of Formula 1 administered in the dose described above beginning on the day of adjuvant injection and continuing for 17 days thereafter, exclusive of days 4, 5, 11 and 12, protect the animals against development of both primary and secondary lesions of adjuvant arthritis.

The pharmaceutical compositions of this invention are prepared in conventional dosage unit forms by incorporating an amount of a compound of Formula 1 sufficient to produce antiarthritic activity, without toxic effects, with a nontoxic pharmaceutical carrier according to accepted procedures. Preferably the compositions will contain as phosphine or phosphite gold Formula 1 in an amount of from about 1.0 mg. to about 10 mg. per dosage unit.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Examplary of liquid carriers are syrup, peanut oil, olive oil, water and the like. Similarly the carrier or diluent may include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form or in the form of a troche or lozenge. The amount of solid carrier will vary sidely but preferably will be from about 25 mg. to about 1 g. If a liquid carrier is used, the preparation will be in the form of a syrup, emulsion, soft gelatin capsule, sterile injectable liquid such as an ampule or nonaqueous liquid suspension.

The pharmaceutical dosage unit forms described hereinabove exclude simple non-sterile solutions of the active medicament in water or in common organic solvents and exclude simple aqueous suspensions of the active medicament in the absence of a suspending agent.

The method in accordance with this invention comprises administering internally to an animal organism a bis[(trialkylphosphine)gold(I)]sulfide compound of Formula 1, usually combined with a pharmaceutical carrier, in an amount sufficient to produce antiarthritic activity without toxic effects. The active medicament will be administered in a dosage unit, preferably in an amount of from about 1.0 mg. to about 10 mg. The route of administration may be orally or parenterally, the oral route being preferred. Advantageously equal doses will be administered one or two times daily with the daily dosage regimen being from about 1.0 mg. to about 12 mg. When the method described above is carried out antiarthritic activity is produced with a minimum of side effects.

The pharmaceutical preparations are made following the conventional techniques of the pharmaceutical chemist involving mixing, granulating and compressing when necessary, or variously mixing and dissolving the ingredients as appropriate to the desired end product.

The following examples illustrate the preparation of compounds of Formula 1 and their incorporation into pharmaceutical compositions of this invention and as such are not to be construed as limiting the invention as set forth in the claims appended hereto.

EXAMPLE 1

A solution of 5.6 g. of triethylphosphinegold chloride in 200 ml. of chloroform is stirred with 3.8 g. of sodium sulfide monohydrate in 80 ml. of water at room temperature. The layers are separated and the chloroform layer is washed with water, dried ($MgSO_4$) and filtered. The volatiles are removed at reduced pressure to yield a yellow solid. The solid is recrystallized from benzene-ether to yield bis[(triethylphosphine)gold(I)]sulfide as a cream colored solid which decomposes at 220° C.

EXAMPLE 2

In like manner using the procedure of Example 1, trimethylphosphinegold chloride and triisopropylphosphinegold chloride were employed as starting materials to yield bis[(trimethylphosphine)gold(1)]sulfide and bis[(triisopropylphosphine)gold(1)]sulfide respectively.

| Ingredients | Mg./Tablet |
|---|---|
| Bis[(triethylphosphine)gold(I)]sulfide | 1.0 |
| Calcium sulfate, dihydrate | 150 |
| Sucrose | 25 |
| Starch | 15 |

| Ingredients | Mg./Tablet |
| --- | --- |
| Talc | 5 |
| Stearic acid | 3 |

The sucrose, calcium sulfate and bis[(triethylphosphine)gold(I)]sulfide are thoroughly mixed and granulated with hot 10% gelatin solution. The wetted mass is passed through a #6 mesh screen directly onto drying trays. The granules are dried at 120° F. and passed through a #20 mesh screen, mixed with the starch, talc and stearic acid and compressed into tablets.

In like manner, the other bis phosphine gold complexes disclosed herein may be formulated into tablets.

One tablet is taken twice a day.

EXAMPLE 4

| Ingredients | Mg./Capsule |
| --- | --- |
| Bis[(trimethylphosphine)gold(I)]sulfide | 5 |
| Magnesium stearate | 5 |
| Lactose | 400 |

The above ingredients are screened through a #40 mesh screen, mixed and filled into #0 hard gelatin capsules.

One capsule is taken once a day.

What is claimed is:

1. A pharmaceutical composition having antiarthritic activity, in dosage unit form, comprising a pharmaceutical carrier and an effective, nontoxic amount of a bis[(trialkylphosphine)gold(I)]sulfide of the formula:

$$(R_3P{\rightarrow}Au)_2S$$

in which:
R is lower alkyl being straight or branched chain of from one to four carbons.

2. A pharmaceutical composition according to claim 1 in which R is ethyl.

3. The method of producing antiarthritic activity which comprises administering internally to an animal organism in an amount to produce said activity a bis[(trialkylphosphine(gold(I)]sulfide of the formula:

$$(R_3P{\rightarrow}Au)_2S$$

in which:
R is lower alkyl being straight or branched chain of from one to four carbons.

4. The method according to claim 3 in which R is ethyl.

* * * * *